(12) United States Patent
Jeney et al.

(10) Patent No.: US 7,294,488 B2
(45) Date of Patent: Nov. 13, 2007

(54) AMPLIFICATION-HYBRIDISATION METHOD FOR DETECTING AND TYPING HUMAN PAPILLOMAVIRUS

(75) Inventors: Csaba Jeney, Budapest (HU); Tibor Takács, Pilisjászfalu (HU)

(73) Assignee: Genoid KFT (HU)

( * ) Notice: Subject to any disclaimer, the term of this patent is extended or adjusted under 35 U.S.C. 154(b) by 0 days.

(21) Appl. No.: 10/507,556

(22) PCT Filed: Mar. 10, 2003

(86) PCT No.: PCT/HU03/00020

§ 371 (c)(1),
(2), (4) Date: May 11, 2005

(87) PCT Pub. No.: WO03/076667

PCT Pub. Date: Sep. 18, 2003

(65) Prior Publication Data

US 2005/0250092 A1    Nov. 10, 2005

(30) Foreign Application Priority Data

Mar. 14, 2002 (HU) .................................. 0200981

(51) Int. Cl.
*C12P 19/34* (2006.01)
*C12Q 1/68* (2006.01)
*C07H 21/04* (2006.01)

(52) U.S. Cl. .................. 435/91.2; 435/6; 536/24.3; 536/24.33

(58) Field of Classification Search .................. None
See application file for complete search history.

(56) References Cited

U.S. PATENT DOCUMENTS

| | | | |
|---|---|---|---|
| 4,683,195 A | | 7/1987 | Mullis et al. |
| 4,683,202 A | | 7/1987 | Mullis |
| 4,889,818 A | | 12/1989 | Gelfand et al. |
| 4,965,188 A | | 10/1990 | Mullis et al. |
| 5,840,306 A | * | 11/1998 | Hofmann et al. ........ 424/192.1 |
| 6,214,979 B1 | | 4/2001 | Gelfand et al. |
| 6,482,588 B1 | * | 11/2002 | Van Doorn et al. ............. 435/5 |

FOREIGN PATENT DOCUMENTS

| | | |
|---|---|---|
| EP | 0 243 221 | 3/1987 |
| EP | 0 294 659 | 5/1988 |
| WO | 90/02821 | 3/1990 |
| WO | WO99/14377 | 9/1998 |
| WO | WO 9914377 A2 * | 3/1999 |

OTHER PUBLICATIONS

Kleter, B. et al. Novel short-fragment PCR assay for highly sensitive broad-spectrum detection of anogenital human papillomavirus. American Journal of Pathology. (1998) vol. 153. pp. 1731-1739.*

Kleter et al. (1999) Development and clinical evaluation of a highly sensitive PCR-reverse hybridization line probe assay for detection and identification of anogenital human papillomavirus. Journal of Clinical Microbiology. 37(8): 2508-2517.*
GenBank Accession No. X67161 (1996). 3 pages including revision history. Accessed Jul. 27, 2006.*
Buck et al. (1999) Design strategies and performance of custom DNA sequencing primers. Biotechniques. 27(3): 528-536.*
GenBank Accession No. M74117 (1993). 7 pages including revision history. Accessed Jul. 27, 2006.*
GenBank Accession No. AF067160 (1999). 2 pages. Accessed Jul. 27, 2006.*
Yoshikawa et al. Detection and typing of multiple genital human papillomaviruses by DNA amplification with consensus primers. Japanese Journal of Cancer Research (1991) 82: 524-531.*
Forslund et al. A broad range of human papillomavirus types detected with a general PCR method suitable for analysis of cutaneous tumours and normal skin. Journal of General Virology (1999) 80: 2437-2443.*
Kleter et al., "Development and Clinical Evaluation of a Highly Sensitive PCR-Reverse Hybridization Line Probe Assay for Detection and Identification of Anogenital Human Papillomavirus," *J. Clin. Microbiol.*, Aug. 1999, 2508-2517.
Kleter et al., "Novel Short-Fragment PCR Assay for Highly Sensitive Broad-Spectrum Detection of Anogenital Human Papillomavirus," *Am. J. Path.*, vol. 153(6), Dec. 1998, 1731-1739.
Gravitt et al., "Genotyping of 27 Human Papillomavirus Types by Using L1 Consensus PCR Products by a Single-Hybridization, Reverse Line Blot Detection Method," *J. Clin. Microbiol.*, Oct. 1998, pp. 3020-3027.
Snijders et al., "The use of general primers in the polymerase chain reaction permits the detection of a broad spectrum of human papillomavirus genotypes," *J. Gen. Viro.*, vol. 71, 173-181, (1990).
Jacobs et al., "Group-Specific Differentiation between High- and Low-Risk Human Papillomavirus Genotypes by General Primer-Mediated PCR and Two Cocktails of Oligonucleotide Probes," *J. Clin. Microbiol.*, vol. 33(4), 1995, 901-905.
E.M. de Villiers et al., *Molecular Cloning of Viral DNA from Human Genital Warts*, Journal of Virology, Dec. 1981, 40:932-935.
K. Dartmann et al., *The Nucleotide Sequence and Genome Organization of Human Papilloma Virus Type II*, Journal of Virology, 1986, 151:124-130.
K. Seedorf et al., *Human Papillomavirus Type 16 DNA Sequence*, Journal of Virology, 1985, 145:181-185.
S.T. Cole et al., *Nucleotide Sequence and Comparative Analysis of the Human Papillomavirus Type 18 Genome*, J. Mol. Biol., 1987, 193:599-608.
M. Goldsborough et al., *Nucleotide Sequence of Human Papillomavirus Type 31: A Cervical Neoplasia-Associated Virus*, Journal of Virology, 1989, 171:306-311.

(Continued)

*Primary Examiner*—Jeffrey Fredman
*Assistant Examiner*—Angela Bertagna
(74) *Attorney, Agent, or Firm*—Kirkpatrick & Lockhart Preston Gates Ellis LLP

(57) ABSTRACT

The present invention provides amplification and hybridisation method for detecting and typing human papillomavirus (HPV), and the primers and hybridisation probes used in the method. The invention relates to a concrete part of the HPV genome, which is suitable for designing HPV genus-specific and HPV genotype-specific hybridisation oligonucleotide probes.

8 Claims, No Drawings

OTHER PUBLICATIONS

S. Cole et al., *Genome Organization and Nucleotide Sequence of Human Papillomavirus Type 33, Which is Associated with Cervical Cancer*, Journal of Virology, Jun. 1986, 58:991-995.

M. Favre et al., *Two New Human Papillomavirus Types (HPV54 and 55) Characterized from Genital Tumours Illustrate the Plurality of Genital HPVs*, Int. J. Cancer, 1990, 45:40-46.

A. Lörincz et al., *Human Papillomavirus Type 56: a New Virus Detected in Cervical Cancers*, J. Gen. Virol., 1989, 70:3099-3104.

H. Yoshikawa et al., *Detection and Typing of Multiple Genital Human Papillomavirus by DNA Amplifications with Consensus Primers*, Jpn. J. Cancer Res., May 1991, 82(5):524-531 Abstract.

D. Wu et al., *The Ligation Amplification Reaction (LAR)—Amplification of Specific DNA Sequences Using Sequential Rounds of Template-Dependent Ligation*, Genomics, 1989, 4:560-569.

D.Y. Kwoh et al., *Transcription-Based Amplification System and Detection of Amplified Human Immunodeficiency Virus Type I with a Bead-Based Sandwich Hybridization Format*, Proc. Natl. Acad. Sci. USA, Feb. 1989, 86:1173-1177.

J. Guatelli et al., *Isothermal, in vitro Amplification of nucleic acids by a Multienzyme Reaction Modeled After Retroviral Replication*, Proc. Natl. Acad. Sci. USA, Mar. 1990, 87:1874-1878.

F.R. Kramer et al., *Replicatable RNA Reporters*, Nature, Jun. 1989, 339:401-402.

M. Jacobs et al., *A General Primer GP5+/GP6+-Mediated PCR-Enzyme Immunoassay Method for Rapid Detection of 14 High-Risk and 6 Low-Risk Human Papillomavirus Genotypes in Cervical Scrapings*, Journal of Clinical Microbiology, Mar. 1997, 35:791-795.

S.Y. Chan et al., *Analysis of Genomic Sequences of 95 Papillomavirus Types: Uniting Typing, Phylogeny, and Taxonomy*, Journal of Virology, May 1995, 69:3074-3083.

J. Cope et al., *Comparison of the Hybrid Capture Tube Test and PCR for Detection of Human Papillomavirus DNA in Cervical Specimens*, Journal of Clinical Microbiology, Sep. 1997, 35:2262-2265.

W. Qu et al., *PCR Detection of Human Papillomavirus: Comparison Between MY09/MY11 and GP5+/GP6+Primer Systems*, Journal of Clinical Microbiology, Jun. 1997, 35:1304-1310.

A. Stewart et al., *Intratype Variation in 12 Human Papillomavirus Types: a Worldwide Perspective*, Journal of Virology, May 1996, 70:3127-3136.

* cited by examiner

# AMPLIFICATION-HYBRIDISATION METHOD FOR DETECTING AND TYPING HUMAN PAPILLOMAVIRUS

CROSS-REFERENCE TO RELATED APPLICATIONS

This application is the national phase of International (PCT) Patent Application Serial No. PCT/HU03/00020, filed Mar. 10, 2003, published under PCT Article 21(2) in English, which claims priority to and the benefit of Hungarian Patent Application No. P0200981, filed Mar. 14, 2002, the disclosure of which is incorporated herein by reference.

FIELD OF THE INVENTION

In the present invention method is provided for improved detection and genotyping human papillomavirus (HPV). One aspect of the invention defines HPV genomic regions, which are suitable for designing HPV genus-specific and HPV genotype-specific hybridization oligonucleotide probes, advantageously are close to each other and in one amplicon.

Another aspect of the invention relates to the sequences of the genus-specific and genotype-specific probes.

Another aspect of the invention relates to optimised formulation of reagents and method, which is suitable to amplify and detect an expanded set of HPV genotypes ("kit").

BACKGROUND OF THE INVENTION

Numerous papillomavirus sequences were determined, see the publications incorporated herein by reference: HPV-6: de Villiers et al., J. Virology, 40 (1981); HPV-11: Dartmann et al., Virology 151, 124-130 (1986); HPV-16: Seedorf et al., Virology 145, 181-185 (1985); HPV-18: Cole and Danos, Journal of Molecular Biology 93, 599-608 (1987); HPV-31: Goldsborough et al., Virology 171, 306-311 (1989); HPV-33: Cole and Streeck, J. Virology, 58, 991-995 (1986); HPV-54: Favre et al., J. Cancer 45, 40-46 (1990); HPV-56: Lőrincz, J., Gen. Virol. 70, 3099 (1989).

Detecting and typing of HPV is reported in a number of publications, besides Soutern blotting and other hybridisation techniques, the most widely used techniques are the PCR-based methods, since these methods simultaneously provide high sensitivity, specificity and the flexibility of the assay gives more control to comply the analytical requirements.

Human papillomavirus, a member of the Papillomaviridae family, is a DNA tumorvirus, with an 8000 bp of circular genome. The virus shows strong epithelial tropism, and proliferates only in differentiated epithelial cells. The papillomavirus has suspected etiologic role in many different human diseases, for example in different skin diseases, i.e. in verruca, condyloma acuminatum and skin tumours and in other conditions, such as cervical carcinoma, anogenital carcinomas, laryngeal carcinoma. It is well established that the human papillomavirus shows strong correlation with the incidence of these tumors, and this is even true for the pre-cancerous lesions (CIN, VIN, VAIN, PIN, PAIN). HPV can be detected in 99% of the cervical carcinoma patients. This close statistical relationship is possibly caused by the causal role of the HPV in the formation of cervical carcinoma. On the basis of the epidemiological data, the patients to be infected by different HPV genotypes do not have the same level of risk to develop cervical carcinoma. According to these findings the genotypes are classified into low risk, medium risk and high risk classes, and besides these there are not-classified genotypes too. Since the risks are grossly different and the incidence of the HPV infection is very high, the determination of genotype is of great importance.

The HPV virus can not be cultivated. The serological diagnosis of HPV infection is limited to detect the exposure to the virus (past or present infection), but can not exactly identify the genotype, the role is mostly limited to epidemiological investigations.

For papillomaviruses, exact serologic classification (serotyping) does not exist genotyping is the widely accepted classification method. These can be divided into two groups, according to whether detection is preceded by amplification or not. In one embodiment of the latter method, full length genomic RNA probes are used to detect the denatured HPV DNA genomes, and the heteroduplex is detected with specific antibodies (Hybrid Capture—Digene). According to another method, Southern blot technique is used for detection and genotyping the HPV genotypes. The disadvantage of these methods is the relative insensitivity and partial lack of specificity. In the case of the Hybrid Capture method many publications report different cross-reactions, causing false positive reactions in clinical conditions. The authors reported that the cross-reactions were acceptable only with a cut-off control of high (1 ng/ml) DNA concentration, which underlines the non-desirable coupling between sensitivity and specificity.

By the amplification methods this problem does not appear, since the reaction responsible for the sensitivity (amplification) is carried out separately.

Generally the amplification techniques differ in the selected amplified genome segment, number of primers, and the applied detection technique. The most frequently used primers are the GP5+-GP6+, MY9-MY11 and the different type-specific PCR reactions.

The most frequently used detection techniques are the sequence-specific hybridisation, restriction fragment length polymorphism (RFLP) and the line probe assay (LiPA). Besides these ones, sequencing of amplicons and thymidine pattern generated by dUTP incorporation is used, but less frequently.

The analytical characteristics of the amplification techniques vary in wide ranges. The methods can be characterized by the amplifiable genotypes, the analytical sensitivity of the genotype amplification and the specificity and reliability of the detection. In this field the MY9-MY11 degenerated primer system is considered to be the reference reaction. In case of the MY9-MY11 system LiPA hybridisation detection system exists (Innogenetics). The major drawback of the MY9-MY11 system it is difficult to control the degenerated synthesis of the primers that is why the relative ratio of the primer species produced in the synthesis is varying from synthesis to synthesis, which can result in the unpredictable changes of the analytical behaviour of the PCR reaction; secondly, this reaction can amplify the fewest types, compared to the other widespread used reactions. It is well known from the literature, that the system can amplify genotype 51 only in that case, if the HPV genotype 51 type-specific primers are added to the reaction. Using degenerate primer synthesis the relative ratio of the primer species can not be changed, and it is impossible to tailor the primer ratios to achieve better analytical performance and a balanced amplification of genotypes.

The GP5+-GP6+ reaction solves the problem only by the use of two carefully selected pair of primers—optimised to the genital HPV sequences—the two primer systems are easy to manage, however the flexibility is lower. The GP5+-GP6+ system can amplify a lot of known HPV genotypes, but the analytical characteristics of the system are not optimal (sensitivity is not balanced with different genotypes), and the two primer approach is constrained in optimisation, e.g. balancing the detection sensitivities for the individual genotypes is highly problematic (except the limited optimisation of the melting temperature and concetration of the $MgCl_2$). It is difficult to adapt the GP5+-GP6+ system to the amplification of other genotypes, which in any case influence its future application, since the need for detecting new genotypes permanently occur. The identification of the genotypes is not solved adequately.

Another well known wide genotype-specific amplification method is the L1C method: two-primer system, with two versions, one is using (with the LC1 primer) the L1C2 or the new L1C2 primer, to amplify further genotypes. The detailed description of the L1C amplicon can be found in the literature [Jpn. J. Cancer Research 82, 524-531 (1991)].

Basically two criteria must be fulfilled by the detection postamplification methods: routine diagnostic applicability (simplicity, costs, time), and the requirement of power of discrimination suitable level of discrimination power. A significant group of methods are not suitable in terms of power of discrimination discrimination power. Therefore the application of the RFLP is limited, because of the short amplified regions, there are not enough diagnostic restriction sites, so often the genotypes can only be classified into groups. Another example the SSCP technique is difficult to refer the complex patterns of the SSCP to genotypes, and also, the robustness of these reactions is not satisfactory, either.

The power of discrimination is especially important from the diagnostic point of view to fulfil the requirements of the regulatory authorities. From the aspects of the simplicity and the power of discrimination sequencing is the ideal approach, since its automation is solved and able to detect each genotypes (or even subtypes thereof), if the sample is not a mixture of genotypes. But in the practice it is not widely used, because it is expensive and time-consuming, and its application in routine diagnostic laboratories is not acceptable, and in case of mixed samples none of the genotypes can be determined.

The advantage of the hybridisation methods is that their power of discrimination or stringency can easilybe changed, since several parameters of the reaction can be varied in wide ranges, and some forms are easily automated, the reaction is less expensive, and in case of parallel implementation (with some forms) even the time needed is insignificant.

Therefore there is a need for a new HPV amplification/detection method, which eliminates the disadvantages of the current methods, and it is cheap, easy to reproduce and automate. The invention describes an amplification and hybridisation assay, in which the primers are independently synthesized molecules, therefore their relative ratio can easily be controlled and optimised, and the amplification has a balanced sensitivity. Hybridisation reactions carried out in highly parallel manner comply with the criteria of a low cost, fast, flexible and automatable reaction.

SUMMARY OF THE INVENTION

In one aspect the present invention provides/defines a human papillomavirus genomic regions, which is inside a consensus amplicon (that is a region, which is amplifiable with primers binding to conserved sequences flanking the amplicon), wherein these genomic regions are characterised having genotype specific DNA sequence, which is suitable to design genotype specific hybridisation probes.

In Another aspect, the invention provides/defines an another HPV genomic region in this consensus amplicon, wherein these genomic regions are characterised having HPV genus specific, conserved DNA sequence, which is suitable to design genus specific hybridisation probes.

An essential element the invention is the presence of two genomic segments inside one consensus amplicon, which are suitable for designing genus and genotype specific hybridisation probes.

In Another aspect, the invention provides the use of primers in amplification reaction, the DNA sequences and concentrations of which, and the conditions of the reaction-cycle to be optimised for the balanced sensitivity amplification of the human papillomavirus genotypes.

The present invention provides methods for detecting and genotyping the human papillomavirus (HPV), wherein the methods comprise the steps of:

a) nucleic acid molecules isolated from biological samples are amplified with the primer mixture of the invention, and as a result double-stranded, amplified products are produced, which b1) are either hybridised in stringent conditions with the HPV genus specific hybridisation probe, or with a mixture thereof, and the presence of HPV consensus amplicon present in a given case are detected;

and/or b2) are hybridised in stringent conditions with a mixture of the genotype specific hybridisation probes provided by of the invention, and the corresponding HPV genotype-groups are detected;

and/or b3) are either hybridised in stringent conditions with a type-specific hybridisation probe of the invention or a mixture of thereof, and the HPV genotype present in a given case are detected and determined.

In summary the method provided in present invention can be used for the amplification/detection of a given group of the HPV genotypes, resulting in the detection of HPV genomic DNA thereof with genus specific probes, and the collective (grouped) or individual genotyping of the HPV genomes. The method can be used to access the risk or to determine those individuals who are at risk of later conditions and diseases, caused or associated by the HPV viruses found in the patients, at a given time, and especially with the type-specific detection thereof. The method provided by the invention is also suitable to screen for the presence of HPV in a given population and also to augment, support or confirm a cytological diagnosis in a given individual (screening).

DETAILED DESCRIPTION OF THE INVENTION

To aid in understanding the invention, several terms are defined below.

The terms "nucleic acid" and "oligonucleotide" refer to probes, primers, and other short DNA, RNA, PNA (peptide nucleic acid) and other chemical oligomers, which are capable of sequence-specific binding on DNA, RNA or PNA template (target molecule).

The term "hybridisation" refers to the sequence-specific binding of two nucleic acid sequences. The conditions used significantly determine the stringency of hybridisation, therefore hybridisation can occur under less stringent conditions, even if the nucleic acids are not exactly complementary. In some cases it could be necessary that the nucleic acid probe bind to a group of sequences, which are closer or farther relatives of each other. Those skilled in the art of nucleic acid technology can determine the conditions, which if fulfilled, then binding is suitably specific or aspecific.

The term "probe" refers to a set of oligonucleotides, which show sequence-specific hybridisation in the presence of complementary and partially complementary nucleic acids. The structure of the oligonucleotides can be modified, to make execution of the steps following hybridisation possible, or to change their hybridisation properties.

The term "type-specific probe" refers to a set of oligonucleotides, which under stringent conditions bind only to the target region that is exactly complementary with them. Hybridisation conditions suitable for this requirement are well known in the art (see, e.g., Sambrook et al., 1985, Molecular Cloning Laboratory Manual, Cold Spring Harbor Laboratory, Cold Spring Harbor, N.Y. USA). Generally, stringent conditions are selected to be about 5° C. lower than the thermal melting point (Tm) for the specific sequence at a defined ionic strength and pH. The Tm is the temperature (under defined ionic strength and pH) at which 50% of the probe is associated in the presence of the suitable complementary target molecule. Relaxing the stringency of the hybridising conditions (for example raising salt concentration or lowering temperature) will allow bindings of not exactly complementary sequences. In case of not exactly complementary template, the nucleotides, which can not bind to the template nucleic acid in the template are the "mismatch nucleotides".

The term "primer" refers to nucleotides, capable of acting as a point of initiation of DNA synthesis (priming) under conditions in which synthesis of a primer extension product complementary to a nucleic acid strand is induced on a nucleic acid template, i.e., in the presence of four different nucleoside triphosphates and an agent for polymerisation (i.e., DNA polymerase or reverse transcriptase) in an appropriate buffer and at a suitable temperature. A primer is preferably a single-stranded DNA molecule. The appropriate length of a primer typically ranges from 15 to 40 nucleotides. A primer does not need to reflect the exact sequence of the template, therefore by changing the temperature of the binding (reaction) group of similar target molecules can serve as template for the synthesis (consensus amplicon). Chemical groups with certain advantageous characteristics can be used to label the primer oligonucleotide, to make it capable for binding to solid phase and for other purposes.

The term "primer"—in the present invention—also refers to a group of sequentially related oligonucleotides, wherein the group of oligonucleotides is capable for priming (as described above) on a certain group of template sequences. Additionally, members of the group may consist of oligonucleotides which may form mismatches with some or all members of a given set of template nucleic acids. But under appropriate conditions these primers can also participate in the priming. The term "consensus primers" refers to a primer or group of primers, which can be used for the priming of certain regions of related template nucleic acids. The characteristic of these regions is that their variability is significantly lower than the variability of the whole nucleic acid, i.e. they are conserved, therefore on these sequences selected consensus primers can do priming including the whole group of template nucleic acid sequences. The consensus primer is not necessarily a single primer, it can be a group of primers.

The term "thermostable polymerase enzyme" refers to an enzyme that is relatively stable at 95° C. and catalyses the polymerisation of nucleoside triphosphates to form primer extension products that are complementary to one of the nucleic acid strands of the target sequence. A purified thermostable polymerase enzyme is described in U.S. Pat. No. 4,889,818, incorporated herein by reference, and is commercially available for example from Applera.

In the present invention amplification of DNA is carried out by the polymerase chain reaction (PCR), disclosed in U.S. Pat. Nos. 4,683,195, 4,683,202, and 4,965,188.

In the present invention optimised PCR conditions have developed for the purposes of the amplification of large number of different HPV genotypes with optimisation of primer concentrations, primer sequences and cycling conditions. First part of the amplification amplifies with constantly growing stringency, with the goal, that the amplification of the genotypes, for which the primers contain more mismatch nucleotides, could start to amplify with the same efficacy than the other genotypes, but later the growing binding temperature shifts the reaction towards the use of the primers, which are in larger quantities. With an optimised mixture of primers this process—in theory—will shift the primer binding sequences toward a consensus sequence, thus creating the possibility for the balanced sensitivity amplification of the genotypes.

Although the polymerase chain reaction is the preferred amplification method, the mentioned genomic regions and oligonucleotides can be used in any known method. For example the ligase chain reaction (Wu and Wallace 1989, Genomics 4:560-569), the TAS amplification system (Kwoh et al., 1989, Proc. Natl. Acad. Sci. USA 86:1173-1177), and self-sustained sequence replication (Guatelli et. al., 1990, Proc. Natl. Acad. Sci. USA 87:1874-1878) can also be suitable for the correct amplification of the target sequence. Similarly, in the Q-beta-replicase system (Kramer and Lizardi, 1989, Nature 339:401-402) sequence-specific probes can be amplified.

In the present invention the primers are chosen form group a more or less complematray sequences suitable to amplify HPV consensus amplicons. Effective priming is achived in the presence of mismatch nucleotide using carfully designed annealing temperature and relative concentrations of the primers.

In a preferred embodiment of the present invention, the primers of the invention (SEQ. ID. NO: 1-40, 70-72) are used with the known primers (SEQ. ID. NO: 73-75) in the form of suitable reagents. This allows the detection of an extended set of HPV genotypes, at least 47 known genotypes. It can be seen in example 4, that the amplification of the HPV-35 genotype according to the invention can be carried out including the primer SEQ. ID. NO. 37 in the reaction. Without this primer including only the known primers in the reaction the HPV-35 genotype is not amplified. Another aspect of the invention relates to type-specific primers for the HPV L1 gene, which include one of the nucleotide sequences described in SEQ. ID. NO: 1-36 sequences.

Another aspect of the invention relates to the mixture of primers including the L1C1, L1C2 or new L1C2 primers and primers which are chosen form SEQ. ID. NO: 1-40, 70-72 Moreover, the invention relates to the application of such mixture of primers for the amplification of HPV 3, 4, 6, 7, 9, 10, 11, 12, 13, 14, 16, 18, 20, 24, 26, 28, 29, 30, 31, 32, 33, 34, 35, 36, 39, 39, 40, 41, 42, 44, 45, 51, 52, 53, 54, 55, 56, 58, 25 49, 60, 61, 66, 67, 68, 72, 74 or 77 genotypes.

Another aspect of the invention relates to the amplicons produced by amplification using the mixture of primers of the invention, mentioned above, with the exception of the HPV-6, -11, -16, -18, -31, -33, -42, -52, and -58 amplicons.

An essential element of the present invention is the presence of the generic and type-specific genomic segments in the amplicons. These genomic segments enable realisation of the highly specific hybridisation and detection. Therefore the present invention relates also to a genomic segment of the amplicons, characterised by a genotype-specific, diverse genomic segment stretching from the 3' end of the amplicon (in 3'-5' direction) from the −80 bp to −30 bp. These genomic segments are about 40 bp long, double-stranded DNA sequences, given in the SEQ. ID. NO: 77, 79, 81, 83, 85, 87, 89, 91, 93, 95, 97, 99, 101, 103, 105, 107, 109, 111 sequences.

Another aspect of the present invention relates to another genomic segment of the amplicons, stretching 3'-5' from the 3' end of the amplicon from the −150 bp to −105 bp, and characterised by highly conserved low complexity sequences between genotypes, which shows generic HPV genus specificity. These genomic segments are double-stranded DNA, usually contain 23 bp, and their upper strand has one of the following sequences: SEQ. ID. NO: 76, 78, 80, 82, 84, 86, 88, 90, 92, 94, 96, 98, 100, 102, 104, 106, 108, 110.

During hybridisation detection of the amplicons, generic or type-specific hybridisation probes are used, designed for the genomic segments mentioned above. The generic oligo-nucleotide probes are generally applicable for detection of the HPV amplicon, that is the amplified HPV DNA, while the type-specific probes can be used for further typing thereof, that is for detecting the individual genotypes. Both hybridisation probes can be DNA, RNA or PNA in nature.

The generic probes used in the method of the invention have similar properties to the consensus primers, with the difference, that the 5' end is not preferred for the position of mismatch nucleotide pairs. In present invention they are used as probes, these generic probes can be used both as hybridisation probes and primers.

Therefore the invention relates to the generic (consensus) hybridisation probes or primers, which include one of the sequences listed in the SEQ. ID. NO: 41-49 sequences.

In a preferred method of the invention the following probes are used as generic probes: SEQ. ID. NO: 41-49.

In case of type-specific probes the probes are 100% complementary to the sequence of the corresponding genotype. During their design it is important to exclude the possibility, whether other genotypes show high level complementary with the probe or part of it. Since the type-specific segment is about 40 bp long in the amplicons of the invention, it is possible to select even overlapping probe-sequences, which are the most adequate both theoretically and experimentally. It is demonstrated in Example 5 that adequate probes could be designed and used, which have high specificity (compared to the investigated 70 genotypes), and they keep their specificity even at room-temperature with the hybridisation conditions used. Since the hybridisation of probes is suitably specific in identical hybridisation conditions, the mixture of the probes can also be used. Therefore from practical point of view more uniform reaction conditions can be used. Therefore the invention relates to the sequences of the type-specific probes, which can be used in HPV amplification and detection and genotyping tests, and include one of the sequences listed in SEQ. ID. NO: 50-67.

Although the invention relates to any embodiment of the hybridisation, but commercially the solid phase hybridisation is preferred.

The so called solid phase (forward) hybridisation binds the probes to immobilized target nucleic acid (amplicon), while the reverse hybridisation binds the target nucleic acid (amplicon) to immobilized probes. Unbound reaction products are removed with different washing solutions in the process. In the first case the probe must be labelled suitably for later development, while in the reverse form the amplicon labelled. Both systems can be realized in microtiter plates. Since the capacity of immobilization is limited, in the present invention the forward hybridisation system is preferred because of the large number of the individual probes constituting the mixture of probes used.

The method described in U.S. Pat. No. 6,214,979 can similarly be applicable, where the probes are added to the reaction during amplification. During the process the 5'-3' exonuclease activity of the Taq polymerase decomposes the probes, and detecting the produced decomposition products can be used for detecting the presence of the target nucleic acid. But other, mostly hybridisation based, so called real-time detection systems are also known, but these differ only in their implementation and detection method, and not in a theoretically different realization of the sequence-specific probe-amplicon binding.

For the immobilization the amplicons can be labelled. From the various possibilities in the present invention the biotin labelling of the primers and the use of labelled primer in amplification reactions preferred. In the presence of avidin or streptavidin absorbed to solid phase biotin results in the immobilization of the amplicon, as a consequence of the highly specific and very stable avidin-biotin binding. In a given reaction only primers hybridising to one or the other strand are biotinilated, so the other strand can be removed before hybridisation.

For detection purposes the probes can be labelled, which labels can be detected by various methods, for example by detection methods which are based on fluorescence, radioactivity, colorimetry, X-ray diffraction, absorption, magnetism, enzyme activity etc. Therefore the suitable labelling may include but are not limited to the following: fluorophores, chromophores, isotopes, electrodense substances, enzymes or ligands able to form specific binding. Combination of the systems mentioned above can also be used. In the present invention the specific binding of fluorescein with anti-fluorescein-HRPO antibody which is detected by the horseradish peroxidase oxidation reaction in the presence of HPPA substrate and $H_2O_2$ is preferred (see Example 2). In the present invention biotinilated forward or reverse primers are used. Both the labelling of the probes and the anti-fluorescein-HRPO are commercially available. Chemicals necessary for washings and the various solutions are also generally available. System using alkaline phosphatase, or any other enzyme, which activity can be detected, can also be constructed or used Besides the fluorescent detection luminometry and colorimetry are also acceptable detection methods, for medical diagnostic application of the system.

Including internal control during diagnostic application of the method of the invention gives the possibility to recognize false negative reactions and from a diagnostic point of view it is preferred. Various artificial or natural DNA source can be used for internal control. Those systems are preferred, which do not increase the number of the primers used in the reaction, and the amount and analytical properties of the internal control target nucleic acid are suitably standardized. In the present invention an artificial nucleic acid sequence (SEQ. ID. NO: 68) is added to the sample in the form of recombinant plasmid (Example 6). In the present invention detecting of the internal control is carried out parallel with the hybridisation detection of HPV DNA, and only the development of the substrates is separated. The probe is digitoxigenin labelled (SEQ. ID. NO: 69), and detectable with alkaline phosphatase conjugated anti-digitoxigenin antibody. However other detection techniques are also suitable for detection of internal probe.

But detecting of the internal control can also be carried out on the basis of mobility differences, using agarose gel-electrophoresis or other suitable technique.

For the amplification and the detection of the HPV DNA the method of the present invention is suitable to produce a harmonized unit of the reagents (kit). In this form the kit can contain all the following reagents, or any combination of them, and other reagents: primers, mixture of primers, buffers, thermostable polymerase, positive control HPV DNA, non-HPV DNA, internal control DNA, probes or mixture of probes, antibody-enzyme conjugate.

The description of sequences of the primers and probes of the invention is only illustrative. Many variants of both the generic and the type-specific probes can be designed using the generic or type-specific HPV genomic region, for those skilled in the art, therefore the variations as far as they are chosen form the genomic region of the invention are covered by the scope of the present invention.

The invention is presented in more details with the following examples. Although the method, which is the basis of the invention is applicable to the amplification of any HPV genome, in the following examples only the genital HPV genomes are used, which are of greater medical importance. It is to be noted, that the examples are only illustrative, and are not to be construed as limiting the scope of the invention.

EXAMPLE 1

Synthesis of Oligonucleotide Primers

The oligonucleotide primers used in the method of the invention were commercial sources (IDT, USA). The primers were synthesised with a 5' amino group. NHS-ester was used for biotin, fluorescein and digitoxigenin labelling. The labelled nucleotides were HPLC purified.

EXAMPLE 2

Processing of the Specimens, Preparation of DNA

Samples were taken by gynaecologists using cytobrush, samples are transported in PBS (10 mM Phosphate buffered Saline pH=7.4, Sigma, NaCl 138 mM, KCl 2.7 mM) solution. Pre-treatment of the samples was done in the sampling tubes: before lysing, the samples were centrifuged (2000 g, 10 minutes), supernatants were discarded, and 1 ml PBS solution was added, vortexed, centrifuged again, discarding the supernatant. In the end of the process 250 µl lysing solution was added to the samples (0.5 mg/ml proteinase-K, 0.01 M TRIS-HCl pH=8, 0.001 M EDTA pH=8, in distilled water), which solution contains the internal control of the HPV test (SEQ. ID. NO: 68), and vortexed and incubated for 30 minutes at 56° C. From this point all liquid handling tasks were carried out on a TECAN RSP150 robot.,:. 200 µl binding solution (5.5 M GUSCN, 20 mM EDTA, 10 mM TRIS-HCl pH=6,5, 65 mM ditiothreitol, 40 g/l silica, SIGMA Cat. No.: 28,851-3, distilled water) was added, and the silica was separated by vacuum filtration from the soluble components. Filtration is used again to wash the silica twice with 200 µl binding solution without silica (5.5 M GUSCN, 20 mM EDTA, 10 mM TRIS-HCl pH=6,5, 65 mM ditiothreitol, distilled water), and 200 µl washing solution is used twice (25% isopropyl-alcohol, 25% 96%-ethanol, 50% distilled water, 0.1 M NaCl), finally with 200 µl 96%-ethanol is applied. After air drying the silica, DNA was eluted in 200 µl 10 mM TRIS-solution pH=8.0. Eluted DNA is stored frozen at −20° C. until further use.

EXAMPLE 3

General Description of the HPV Detection Amplification

The total reaction-volume was 25 µl, including the following components: 10 µl DNA, 2.5 µl 10× polymerase buffer (final concentration: 10 mM TRIS-HCl (pH=9,0), 50 mM KCl, 0.1% Triton X-100 (Promega)), 2 mM $MgCl_2$, 250 µM each dNTP (ATP, CTP, GTP, TTP), 4 µM of a primer-mixture: SEQ. ID. NO: 35, 37-40, 73-75, and 1U Taq DNA polymerase (Promega). The reaction was carried out in GeneAmp 9700 PCR thermal cycler, with the following parameters:
Cycle 1: 4 minutes at 95° C.;
Cycles 2-40: 30 seconds at 94° C., 1 minute at 48° C., and 45 seconds at 72° C.;
Cycle 41: 3 minutes at 72° C.

Hybridisation and Detection

Hybridisation was carried out on solid phase. 24 hours earlier the black, 96-well polystyrene plates (Costar) were coated with streptavidin (0.02 mg/ml streptavidin in PBS solution). Plates were incubated at room temperature, and 24 hours later the plates were washed twice with 250 µl washing solution [25 mM TRIS pH=7.5, 125 mM NaCl, 20 mM $MgCl_2$, 3% Tween-20]. 20 µl of the product of the PCR-reaction is diluted with 140 µl distilled water, and 5 µl from this solution was mixed with 45 µl binding puffer [25 mM TRIS pH=7.5, 125 mM NaCl, 5 mM EDTA-$Na_2$, 5× Denhardt's solution, 0.1% Tween-20] and dispensed into the wells of the streptavidin coated plate. The reaction was incubated at room temperature for 30 minutes, with constant shaking. Then 50 µl elution buffer [100 mM NaOH, 300 mM NaCl] was added to the mixture, incubated for 3 minutes at room temperature, and the plates were washed 3 times with 250 µl washing solution [25 mM TRIS pH=7.5, 125 mM NaCl, 20 mM $MgCl_2$, 3% Tween-20]. After the washing 50 µl hybridisation buffer (5×SSC (0.3 M Na-citrate pH=7, 3 M NaCl), 1× Denhardt's solution, 0.1% SDS], containing fluorescein labelled probes (5 nM per probe) was added to the wells. The mixture was incubated for 30 minutes at 50° C. with constant shaking, and washed 6 times with 250 µl high stringency washing solution [0.05×SSC, 0.3% Tween-20]. After this 50 µl conjugation buffer [25 mM TRIS pH=7.5, 125 mM NaCl, 2 mM $MgCl_2$, 0.3% Tween-20, 1% BSA], containing Anti-Fluorescence-POD (Roche) antibody (0.0015 E/reaction) was added to the reaction. Plates were incubated for 30 minutes at room temperature with shaking, and washed 6 times with 250 µl high stringency washing solution[125 mM TRIS pH=7.5, 125 mM NaCl, 20 mM $MgCl_2$, 3% Tween-20]. For development 135 µl substrate solution (5 volume [45 mM hydroxiphenyl-propionic acid (HPPA), dissolved in 0.1 M TRIS-HCl pH=9.0 buffer], +1 volume [0.6 g/l $H_2O_2$ in 20 mM citrate-phosphate buffer]) was added. To stop the reaction 65 µl stop solution [0.75 M glycine pH=10.3] was added to the reaction mixture after 20 minutes. The fluorescent signal was measured with SpectraMax plate-fluorometer at 324/410 nm. Samples were considered positive if their value was higher than three times of the average of 3 parallel negative control sample value.

EXAMPLE 4

Comparative Study of Amplification

Samples were spiked at 10 ng/reaction by plasmids containing cloned HPV L1 region from different genotypes and used to amplify and detect HPV DNA by method of the invention. PCR reaction and hybridisation was carried out according to the description of Example 3, with the difference that the composition of the primers were changed. The reaction without the L1F2 (SEQ. ID. NO: 37) did not result in amplification with the genotype HPV 35, while using the L1F2 primer resulted in the effective detection of the genotype HPV 35.

EXAMPLE 5

Detecting Several HPV Genotypes

Samples were spiked at 10 ng/reaction by plasmids containing cloned HPV L1 region from different genotypes and used to amplify and detect HPV DNA by method of the invention. PCR reaction and hybridisation was carried out according to the description of Example 3. Amplification and typing of the following HPV genotypes were attempted: 1-24, 26-42, 45, 47-68, 72-74, 76-77, 86. The amplification of the following genotypes were demonstrated with agarose gel-electrophoresis: 3, 6-7, 10-11, 13-14, 16, 18, 20, 24, 26, 29, 30-36, 39-40, 42, 45, 51, 52-55, 58-62, 66-68, 72. Using the mixture of the SEQ. ID. NO: 41-49 genus-specific hybridisation probes (using the conditions described in Example 3) the following genotypes were detectable: 3-4, 6-7, 9-14, 16, 18, 20, 24, 26, 29, 30-37, 39-42, 45, 51, 52-55, 58-62, 66-68, 72, 74, 77. Data show, that a portion of the genotypes can only be detected by hybridisation, which is not surprising, since hybridisation is about 10-100-times more sensitive than agarose gel-electrophoresis. It can also be seen from the data, that the genus-specific hybridisation did detect all agarose gel-electrophoresis positive genotypes indicating its true genus-specific nature.

EXAMPLE 6

Detecting the HPV-35 Type

Samples were spiked at 10 ng/reaction by plasmids containing cloned HPV L1 region from different genotypes and used to amplify and detect HPV DNA by method of the invention. PCR reaction and hybridisation were carried out according to the description of Example 3. Hybridisation probe was the oligonucleotide designed for the genotype HPV 35 (SEQ. ID. NO: 58). The detection of amplicons of the following genotypes was attempted: 3-4, 6-7, 9-14, 16, 18, 20, 24, 26, 29, 30-37, 39-42, 45, 51, 52-55, 58-62, 66-68, 72, 74, 77. The probe detected only the corresponding HPV 35 genotype amplicon.

EXAMPLE 7

HPV Detection with Internal Control

Detection of the samples prepared according to Example 2 was carried out according to Example 3, with the difference that the probe of the internal control labelled with digitoxigenin (its amount was the same as the type-specific probes) was used with the type-specific probes, and the anti-fluorescein-POD and the anti-alp-ALP [1:2000, Jackson Immuno Research] antibodies were simultaneously present in the conjugation step. After the development of the POD reaction (see Example 2), development of ALP was carried out according to the following: the substrate solution was 6.25 mg/100 ml 4-methyl-umbelliferil-phosphate in 100 mM TRIS pH=9.0, 0.5 mM $MgCl_2$ buffer. After the development of the HPPA the microtiter plate was washed once with [25 mM TRIS pH=7,5, 125 mM NaCl, 20 mM $MgCl_2$, 3% Tween-20], and 150 µl substrate solution was added to each reaction wells. After 30 minutes incubation the fluorescent signal was measured with SpectraMax plate-fluorometer at 355/460 nm. Samples were considered positive if their value was higher than three times the average of 3 parallel negative control sample value.

Type-specific probes detected the adequate types only. Detection of the internal control was positive in each reaction, except in those reactions, where strong competition between the HPV amplification and the internal control occurred. There were no inhibited reaction (HPV DNA or internal control DNA amplified in all samples). The internal control adequately excluded the possibility of false negative results.

The invention claimed is:

1. A method for the amplification of the 3, 4, 6, 7, 9, 10, 11, 12 13, 14, 16, 18, 20, 24, 26, 28, 29, 30, 31, 32, 33, 34, 35, 36, 37, 39, 40, 41, 42, 44, 45, 51, 52, 53, 54, 55, 56, 58, 59, 60, 61, 66, 67, 68, 72, 74 and 77 genotypes of the human papillomavirus comprising the steps of providing an amplification primer mixture and amplifying the human papillomavirus genotypes, wherein said primer mixture consists of the L1C1, L1C2, new L1C2 primers (SEQ ID NOS: 73-75), and SEQ ID NOS: 9, 10, 35, 37, 39 and 40.

2. A method for detecting one or more HPV genotypes in a biological sample, the method comprising the steps of:
   a) Preparing one or more amplicons obtainable by using the primer mixture of claim 1 from nucleic acid molecules extracted from the biological sample; and
   b1) Hybridising the amplicon obtained in (a) under highly stringent conditions with an HPV genus specific probe; and/or
   b2) Hybridising the amplicon obtained in (a) under highly stringent conditions with a genotype specific hybridisation probe.

3. The method as claimed in claim 2 wherein said HPV genus specific probe is a hybridisation probe or primer, which is an HPV consensus probe or primer and which hybridises to and is complementary to SEQ ID NO: 41.

4. The method as claimed in claim 2 wherein said genotype specific hybridisation probe is a hybridisation probe, which is HPV genotype-specific, and hybridises to SEQ ID NO: 50.

5. The method of claim 2 wherein the low-and high-risk HPV genotype-groups are detected.

6. The method as claimed in claim 2, further comprising detection of a synthetic oligonucleotide as an internal control.

7. The method of claim 6, wherein SEQ ID NO: 68 sequence is used as the internal control, and for detecting this SEQ ID NO: 69 is used as hybridisation probe.

8. A kit for detecting and typing HPV, which comprises
   i) primers selected from the group consisting of:
      consensus primers for the human papillomavirus (HPV) L1 gene, wherein said primers consist of one of the following nucleotide sequences: SEQ ID NO: 37-40 or SEQ ID NO: 70-72, and
      type-specific primers for the human papillomavirus (HPV) L1 gene, wherein said primers consist of one of the following nucleotide sequences: SEQ ID NO: 1-36;
   ii) an amplification primer-mixture, wherein said mixture consists of the L1C1, L1C2, new L1C2 primers (SEQ ID NOS: 73-75), SEQ ID NOS: 37-40, and SEQ ID NO: 35, and optionally one or more primers selected from the group consisting SEQ ID NOS: 70-72, SEQ ID NOS: 1-34 and 36;
   iii) optionally an internal control primer;
   iv) hybridisation probes selected from the group consisting of:
      a hybridisation probe, which is HPV genotype-specific, and hybridises to one of the sequences of SEQ ID NO: 77, 79, 81, 83, 85, 87, 89, 91, 93, 95, 97, 99, 101, 103, 105, 107, 109, 111; and
      a hybrisation probe or primer, which is an HPV consensus probe or primer, and hybridises to one of the sequences of SEQ ID NO: 76, 78, 80, 82, 84, 86, 88, 90, 92, 94, 96, 98, 100, 102, 104, 106, 108, 110; and
   v) optionally hybridisation probes for detecting the internal control.

* * * * *

SEQUENCE LISTING

<160> NUMBER OF SEQ ID NOS: 120

<210> SEQ ID NO 1
<211> LENGTH: 24
<212> TYPE: DNA
<213> ORGANISM: Artificial Sequence
<220> FEATURE:
<223> OTHER INFORMATION: PCR primer (L1CF6)

<400> SEQUENCE: 1
cgtaaacgta ttcccttatt tttt                                    24

<210> SEQ ID NO 2
<211> LENGTH: 21
<212> TYPE: DNA
<213> ORGANISM: Artificial Sequence

```
<220> FEATURE:
<223> OTHER INFORMATION: PCR primer (L1CR6)

<400> SEQUENCE: 2
caatacaggg tatttaaggt g                                              21

<210> SEQ ID NO 3
<211> LENGTH: 25
<212> TYPE: DNA
<213> ORGANISM: Artificial Sequence
<220> FEATURE:
<223> OTHER INFORMATION: PCR primer (L1CF11)

<400> SEQUENCE: 3
cgtaaacgta ttcccttatt tttta                                          25

<210> SEQ ID NO 4
<211> LENGTH: 21
<212> TYPE: DNA
<213> ORGANISM: Artificial sequence
<220> FEATURE:
<223> OTHER INFORMATION: PCR primer (L1CR11)

<400> SEQUENCE: 4
caatatagag tgtttagggt a                                              21

<210> SEQ ID NO 5
<211> LENGTH: 24
<212> TYPE: DNA
<213> ORGANISM: Artificial sequence
<220> FEATURE:
<223> OTHER INFORMATION: PCR primer (L1CF42)

<400> SEQUENCE: 5
cgtaaacctg taccatattt tttt                                           24

<210> SEQ ID NO 6
<211> LENGTH: 21
<212> TYPE: DNA
<213> ORGANISM: Artificial sequence
<220> FEATURE:
<223> OTHER INFORMATION: PCR primer (L1CR42)

<400> SEQUENCE: 6
cagtacagag tatttagagt t                                              21

<210> SEQ ID NO 7
<211> LENGTH: 24
<212> TYPE: DNA
<213> ORGANISM: Artificial sequence
<220> FEATURE:
<223> OTHER INFORMATION: PCR primer (L1CF44)

<400> SEQUENCE: 7
cgtaaacgtg tttccttgtt tttt                                           24

<210> SEQ ID NO 8
<211> LENGTH: 21
<212> TYPE: DNA
<213> ORGANISM: Artificial sequence
<220> FEATURE:
<223> OTHER INFORMATION: PCR primer (L1CR44)

<400> SEQUENCE: 8
caatataggg tttttaagat g                                              21
```

<210> SEQ ID NO 9
<211> LENGTH: 24
<212> TYPE: DNA
<213> ORGANISM: Artificial sequence
<220> FEATURE:
<223> OTHER INFORMATION: PCR primer (L1CF16)

<400> SEQUENCE: 9
cgtaaacgtt taccatattt tttt                                    24

<210> SEQ ID NO 10
<211> LENGTH: 21
<212> TYPE: DNA
<213> ORGANISM: Artificial sequence
<220> FEATURE:
<223> OTHER INFORMATION: PCR primer (L1CR16)

<400> SEQUENCE: 10
caatacaggg tatttagaat a                                       21

<210> SEQ ID NO 11
<211> LENGTH: 25
<212> TYPE: DNA
<213> ORGANISM: Artificial sequence
<220> FEATURE:
<223> OTHER INFORMATION: PCR primer (L1CF18)

<400> SEQUENCE: 11
cgtaaacgtg ttccctattt ttttg                                   25

<210> SEQ ID NO 12
<211> LENGTH: 21
<212> TYPE: DNA
<213> ORGANISM: Artificial sequence
<220> FEATURE:
<223> OTHER INFORMATION: PCR primer (L1CR18)

<400> SEQUENCE: 12
caatatagag tatttagggt g                                       21

<210> SEQ ID NO 13
<211> LENGTH: 24
<212> TYPE: DNA
<213> ORGANISM: artificial sequence
<220> FEATURE:
<223> OTHER INFORMATION: PCR primer (L1CF31)

<400> SEQUENCE: 13
cgtaaacgtg tatcatattt tttt                                    24

<210> SEQ ID NO 14
<211> LENGTH: 21
<212> TYPE: DNA
<213> ORGANISM: artificial sequence
<220> FEATURE:
<223> OTHER INFORMATION: PCR primer (L1CR31)

<400> SEQUENCE: 14
caatataggg tatttagggt t                                       21

<210> SEQ ID NO 15
<211> LENGTH: 25
<212> TYPE: DNA
<213> ORGANISM: artificial sequence
<220> FEATURE:
<223> OTHER INFORMATION: PCR primer (L1CF33)

```
<400> SEQUENCE: 15
cgtaaacgtt tccatattt tttta                                    25

<210> SEQ ID NO 16
<211> LENGTH: 21
<212> TYPE: DNA
<213> ORGANISM: artificial sequence
<220> FEATURE:
<223> OTHER INFORMATION: PCR primer (L1CR33)

<400> SEQUENCE: 16
caatataggg tttttagggt c                                       21

<210> SEQ ID NO 17
<211> LENGTH: 24
<212> TYPE: DNA
<213> ORGANISM: artificial sequence
<220> FEATURE:
<223> OTHER INFORMATION: PCR primer (L1CF35)

<400> SEQUENCE: 17
cgtaaagcta tcccatattt tttt                                    24

<210> SEQ ID NO 18
<211> LENGTH: 21
<212> TYPE: DNA
<213> ORGANISM: artificial sequence
<220> FEATURE:
<223> OTHER INFORMATION: PCR primer (L1CR35)

<400> SEQUENCE: 18
caatacagag tatttagagt a                                       21

<210> SEQ ID NO 19
<211> LENGTH: 25
<212> TYPE: DNA
<213> ORGANISM: artificial sequence
<220> FEATURE:
<223> OTHER INFORMATION: PCR primer (L1CF39)

<400> SEQUENCE: 19
cgtaaacgta ttccctattt ttttc                                   25

<210> SEQ ID NO 20
<211> LENGTH: 21
<212> TYPE: DNA
<213> ORGANISM: artificial sequence
<220> FEATURE:
<223> OTHER INFORMATION: PCR primer (L1CR39)

<400> SEQUENCE: 20
caatataggg tatttcgcgt g                                       21

<210> SEQ ID NO 21
<211> LENGTH: 25
<212> TYPE: DNA
<213> ORGANISM: artificial sequence
<220> FEATURE:
<223> OTHER INFORMATION: PCR primer (L1CF45)

<400> SEQUENCE: 21
cgtaaacgta ttccctattt ttttg                                   25

<210> SEQ ID NO 22
```

```
<211> LENGTH: 21
<212> TYPE: DNA
<213> ORGANISM: artificial sequence
<220> FEATURE:
<223> OTHER INFORMATION: PCR primer (L1CR45)

<400> SEQUENCE: 22
cagtataggg tgtttagagt a                                              21

<210> SEQ ID NO 23
<211> LENGTH: 24
<212> TYPE: DNA
<213> ORGANISM: artificial sequence
<220> FEATURE:
<223> OTHER INFORMATION: PCR primer (L1CF51)

<400> SEQUENCE: 23
cgtaaacgta taccctattt tttt                                           24

<210> SEQ ID NO 24
<211> LENGTH: 21
<212> TYPE: DNA
<213> ORGANISM: artificial sequence
<220> FEATURE:
<223> OTHER INFORMATION: PCR primer (L1CR51)

<400> SEQUENCE: 24
caatacaggg tatttagggt a                                              21

<210> SEQ ID NO 25
<211> LENGTH: 25
<212> TYPE: DNA
<213> ORGANISM: artificial sequence
<220> FEATURE:
<223> OTHER INFORMATION: PCR primer (L1CF52)

<400> SEQUENCE: 25
gcgtaaacgt tttccatatt ttttt                                          25

<210> SEQ ID NO 26
<211> LENGTH: 21
<212> TYPE: DNA
<213> ORGANISM: artificial sequence
<220> FEATURE:
<223> OTHER INFORMATION: PCR primer (L1CR52)

<400> SEQUENCE: 26
caatacaggg tatttagaat t                                              21

<210> SEQ ID NO 27
<211> LENGTH: 25
<212> TYPE: DNA
<213> ORGANISM: artificial sequence
<220> FEATURE:
<223> OTHER INFORMATION: PCR primer (L1CF56)

<400> SEQUENCE: 27
cgtaaacgta ttccctattt ttttt                                          25

<210> SEQ ID NO 28
<211> LENGTH: 22
<212> TYPE: DNA
<213> ORGANISM: artificial sequence
<220> FEATURE:
<223> OTHER INFORMATION: PCR primer (L1CR56)

<400> SEQUENCE: 28
```

```
tcaatatagg gtatttaggg ta                                             22

<210> SEQ ID NO 29
<211> LENGTH: 25
<212> TYPE: DNA
<213> ORGANISM: artificial sequence
<220> FEATURE:
<223> OTHER INFORMATION: PCR primer (L1CF58)

<400> SEQUENCE: 29
acgtaaacgt tttccatatt ttttt                                          25

<210> SEQ ID NO 30
<211> LENGTH: 21
<212> TYPE: DNA
<213> ORGANISM: artificial sequence
<220> FEATURE:
<223> OTHER INFORMATION: PCR primer (L1CR58)

<400> SEQUENCE: 30
cagtataggg tctttagggt g                                              21

<210> SEQ ID NO 31
<211> LENGTH: 24
<212> TYPE: DNA
<213> ORGANISM: artificial sequence
<220> FEATURE:
<223> OTHER INFORMATION: PCR primer (L1CF59)

<400> SEQUENCE: 31
cgtaaacgtg ttccctattt tttt                                           24

<210> SEQ ID NO 32
<211> LENGTH: 21
<212> TYPE: DNA
<213> ORGANISM: artificial sequence
<220> FEATURE:
<223> OTHER INFORMATION: PCR primer (L1CR59)

<400> SEQUENCE: 32
caatacagag tatttagggt t                                              21

<210> SEQ ID NO 33
<211> LENGTH: 25
<212> TYPE: DNA
<213> ORGANISM: artificial sequence
<220> FEATURE:
<223> OTHER INFORMATION: PCR primer (L1CF66)

<400> SEQUENCE: 33
ccgtaaacgt attccctatt ttttt                                          25

<210> SEQ ID NO 34
<211> LENGTH: 21
<212> TYPE: DNA
<213> ORGANISM: artificial sequence
<220> FEATURE:
<223> OTHER INFORMATION: PCR primer (L1CR66)

<400> SEQUENCE: 34
cagtatagag tgtttagggt a                                              21

<210> SEQ ID NO 35
<211> LENGTH: 24
<212> TYPE: DNA
```

```
<213> ORGANISM: artificial sequence
<220> FEATURE:
<223> OTHER INFORMATION: PCR primer (L1CF68)

<400> SEQUENCE: 35
cgtaaacacc ttccttattt tttt                                          24

<210> SEQ ID NO 36
<211> LENGTH: 21
<212> TYPE: DNA
<213> ORGANISM: artificial sequence
<220> FEATURE:
<223> OTHER INFORMATION: PCR primer (L1CR68)

<400> SEQUENCE: 36
caatacagag tgtttagggt t                                             21

<210> SEQ ID NO 37
<211> LENGTH: 24
<212> TYPE: DNA
<213> ORGANISM: artificial sequence
<220> FEATURE:
<223> OTHER INFORMATION: PCR primer (L1F2)

<400> SEQUENCE: 37
cgtaaagcta taccatattt tttt                                          24

<210> SEQ ID NO 38
<211> LENGTH: 24
<212> TYPE: DNA
<213> ORGANISM: artificial sequence
<220> FEATURE:
<223> OTHER INFORMATION: PCR primer (L1F3)

<400> SEQUENCE: 38
cgtaaacacg ttccatattt tttt                                          24

<210> SEQ ID NO 39
<211> LENGTH: 24
<212> TYPE: DNA
<213> ORGANISM: artificial sequence
<220> FEATURE:
<223> OTHER INFORMATION: PCR primer (L1F4)

<400> SEQUENCE: 39
cgtaaacgtg tttcctattt tttt                                          24

<210> SEQ ID NO 40
<211> LENGTH: 21
<212> TYPE: DNA
<213> ORGANISM: artificial sequence
<220> FEATURE:
<223> OTHER INFORMATION: PCR primer (L1R2)

<400> SEQUENCE: 40
cagtacagag ttttttagaat t                                            21

<210> SEQ ID NO 41
<211> LENGTH: 23
<212> TYPE: DNA
<213> ORGANISM: artificial sequence
<220> FEATURE:
<223> OTHER INFORMATION: genus-specific hybridisation probe (PK1)

<400> SEQUENCE: 41
cgcaccaaca tattttatta tgg                                           23
```

```
<210> SEQ ID NO 42
<211> LENGTH: 23
<212> TYPE: DNA
<213> ORGANISM: artificial sequence
<220> FEATURE:
<223> OTHER INFORMATION: genus-specific hybridisation probe (PK2)

<400> SEQUENCE: 42
cgcacaagca tctattatta tgc                                          23

<210> SEQ ID NO 43
<211> LENGTH: 23
<212> TYPE: DNA
<213> ORGANISM: artificial sequence
<220> FEATURE:
<223> OTHER INFORMATION: genus-specific hybridisation probe (PK3)

<400> SEQUENCE: 43
cgcacaagca tattttatca tgc                                          23

<210> SEQ ID NO 44
<211> LENGTH: 23
<212> TYPE: DNA
<213> ORGANISM: artificial sequence
<220> FEATURE:
<223> OTHER INFORMATION: genus-specific hybridisation probe (PK4)

<400> SEQUENCE: 44
cgcaccagta tattttatca tgc                                          23

<210> SEQ ID NO 45
<211> LENGTH: 23
<212> TYPE: DNA
<213> ORGANISM: artificial sequence
<220> FEATURE:
<223> OTHER INFORMATION: genus-specific hybridisation probe (PK5)

<400> SEQUENCE: 45
cgcacaagca tttactatca tgc                                          23

<210> SEQ ID NO 46
<211> LENGTH: 23
<212> TYPE: DNA
<213> ORGANISM: artificial sequence
<220> FEATURE:
<223> OTHER INFORMATION: genus-specific hybridisation probe (PK6)

<400> SEQUENCE: 46
cgcaccaact acttttacca tgc                                          23

<210> SEQ ID NO 47
<211> LENGTH: 23
<212> TYPE: DNA
<213> ORGANISM: artificial sequence
<220> FEATURE:
<223> OTHER INFORMATION: genus-specific hybridisation probe (PK7)

<400> SEQUENCE: 47
cgtaccagta ttttctacca cgc                                          23

<210> SEQ ID NO 48
<211> LENGTH: 23
<212> TYPE: DNA
<213> ORGANISM: artificial sequence
<220> FEATURE:
```

<223> OTHER INFORMATION: genus-specific hybridisation probe (PK8)

<400> SEQUENCE: 48
cgcacaggca tatattacta tgc                23

<210> SEQ ID NO 49
<211> LENGTH: 23
<212> TYPE: DNA
<213> ORGANISM: artificial sequence
<220> FEATURE:
<223> OTHER INFORMATION: genus-specific hybridisation probe (PK9)

<400> SEQUENCE: 49
cgcaccaaca tatattatca tgc                23

<210> SEQ ID NO 50
<211> LENGTH: 20
<212> TYPE: DNA
<213> ORGANISM: artificial sequence
<220> FEATURE:
<223> OTHER INFORMATION: HPV-6 type-specific hybridisation probe (P6)

<400> SEQUENCE: 50
ttttgttagc ccgttttatg                20

<210> SEQ ID NO 51
<211> LENGTH: 23
<212> TYPE: DNA
<213> ORGANISM: artificial sequence
<220> FEATURE:
<223> OTHER INFORMATION: HPV-11 type-specific hybridisation probe (P11)

<400> SEQUENCE: 51
acaactgttt ttgttaactt ttt                23

<210> SEQ ID NO 52
<211> LENGTH: 20
<212> TYPE: DNA
<213> ORGANISM: artificial sequence
<220> FEATURE:
<223> OTHER INFORMATION: HPV-42 type-specific hybridisation probe (P42)

<400> SEQUENCE: 52
tgtcttattt ggccttttg                20

<210> SEQ ID NO 53
<211> LENGTH: 20
<212> TYPE: DNA
<213> ORGANISM: artificial sequence
<220> FEATURE:
<223> OTHER INFORMATION: HPV-44 type-specific hybridisation probe (P44)

<400> SEQUENCE: 53
gtcttgtttg ctggtcgtat                20

<210> SEQ ID NO 54
<211> LENGTH: 25
<212> TYPE: DNA
<213> ORGANISM: artificial sequence
<220> FEATURE:
<223> OTHER INFORMATION: HPV-16 type-specific hybridisation probe (P16)

<400> SEQUENCE: 54
ctaatatttt gttattgtta ggttt                25

```
<210> SEQ ID NO 55
<211> LENGTH: 19
<212> TYPE: DNA
<213> ORGANISM: artificial sequence
<220> FEATURE:
<223> OTHER INFORMATION: HPV-18 type-specific hybridisation probe (P18)

<400> SEQUENCE: 55
tatcctgctt attgccacc                                                  19

<210> SEQ ID NO 56
<211> LENGTH: 22
<212> TYPE: DNA
<213> ORGANISM: artificial sequence
<220> FEATURE:
<223> OTHER INFORMATION: HPV-31 type-specific hybridisation probe (P31)

<400> SEQUENCE: 56
ggattgtcag atttaggtat gg                                              22

<210> SEQ ID NO 57
<211> LENGTH: 23
<212> TYPE: DNA
<213> ORGANISM: artificial sequence
<220> FEATURE:
<223> OTHER INFORMATION: HPV-33 type-specific hybridisation probe (P33)

<400> SEQUENCE: 57
tttttagcgt tagtaggatt ttt                                             23

<210> SEQ ID NO 58
<211> LENGTH: 25
<212> TYPE: DNA
<213> ORGANISM: artificial sequence
<220> FEATURE:
<223> OTHER INFORMATION: HPV-35 type-specific hybridisation probe (P35)

<400> SEQUENCE: 58
tgctatttta ttagaatctt gtttt                                           25

<210> SEQ ID NO 59
<211> LENGTH: 19
<212> TYPE: DNA
<213> ORGANISM: artificial sequence
<220> FEATURE:
<223> OTHER INFORMATION: HPV-39 type-specific hybridisation probe (P39)

<400> SEQUENCE: 59
accaccattc atacccact                                                  19

<210> SEQ ID NO 60
<211> LENGTH: 20
<212> TYPE: DNA
<213> ORGANISM: artificial sequence
<220> FEATURE:
<223> OTHER INFORMATION: HPV-45 type-specific hybridisation probe (P45)

<400> SEQUENCE: 60
acctgcacca ttaggtacaa                                                 20

<210> SEQ ID NO 61
<211> LENGTH: 20
<212> TYPE: DNA
<213> ORGANISM: artificial sequence
<220> FEATURE:
<223> OTHER INFORMATION: HPV-51 type-specific hybridisation probe (P51)
```

```
<400> SEQUENCE: 61
gcgttgaggt tttaggtatt                                              20

<210> SEQ ID NO 62
<211> LENGTH: 21
<212> TYPE: DNA
<213> ORGANISM: artificial sequence
<220> FEATURE:
<223> OTHER INFORMATION: HPV-52 type-specific hybridisation probe (P52)

<400> SEQUENCE: 62
caattaccac tactggtgtt t                                            21

<210> SEQ ID NO 63
<211> LENGTH: 21
<212> TYPE: DNA
<213> ORGANISM: artificial sequence
<220> FEATURE:
<223> OTHER INFORMATION: HPV-56 type-specific hybridisation probe (P56)

<400> SEQUENCE: 63
tgtttgtttt ggtattgtcc t                                            21

<210> SEQ ID NO 64
<211> LENGTH: 20
<212> TYPE: DNA
<213> ORGANISM: artificial sequence
<220> FEATURE:
<223> OTHER INFORMATION: HPV-58 type-specific hybridisation probe (P58)

<400> SEQUENCE: 64
gttattggga cttttgatgg                                              20

<210> SEQ ID NO 65
<211> LENGTH: 20
<212> TYPE: DNA
<213> ORGANISM: artificial sequence
<220> FEATURE:
<223> OTHER INFORMATION: HPV-59 type-specific hybridisation probe (P59)

<400> SEQUENCE: 65
tcctgtctac cattaccacc                                              20

<210> SEQ ID NO 66
<211> LENGTH: 20
<212> TYPE: DNA
<213> ORGANISM: artificial sequence
<220> FEATURE:
<223> OTHER INFORMATION: HPV-66 type-specific hybridisation probe (P66)

<400> SEQUENCE: 66
ttggtaccag atttggaaac                                              20

<210> SEQ ID NO 67
<211> LENGTH: 20
<212> TYPE: DNA
<213> ORGANISM: artificial sequence
<220> FEATURE:
<223> OTHER INFORMATION: HPV-68 type-specific hybridisation probe (P68)

<400> SEQUENCE: 67
cccagacata ggaaccttaa                                              20

<210> SEQ ID NO 68
<211> LENGTH: 198
```

<212> TYPE: DNA
<213> ORGANISM: artificial sequence
<220> FEATURE:
<223> OTHER INFORMATION: Inside control oligonucleotide molecule

<400> SEQUENCE: 68
cgtaaacgtt tccctatttt ttttagtcaa tgagacgggt aatgacgata cagtatgacg    60
atagagtaga tagatagaga tagataccca tatacagata atgacataga tccccataga   120
cagtttatac agatcagtag cagttttat atatgagatg atgataggac acaccagcaa    180
tatagggtat ttagggta                                                  198

<210> SEQ ID NO 69
<211> LENGTH: 21
<212> TYPE: DNA
<213> ORGANISM: artificial sequence
<220> FEATURE:
<223> OTHER INFORMATION: Inside control amplicon-specific hybridisation
      probe (IC-P1)

<400> SEQUENCE: 69
tgacatagat ccccatagac a                                               21

<210> SEQ ID NO 70
<211> LENGTH: 24
<212> TYPE: DNA
<213> ORGANISM: Artificial sequence
<220> FEATURE:
<223> OTHER INFORMATION: PCR primer (L1F5)

<400> SEQUENCE: 70
cgtaaacgta ttccctatttt tttt                                           24

<210> SEQ ID NO 71
<211> LENGTH: 24
<212> TYPE: DNA
<213> ORGANISM: artificial sequence
<220> FEATURE:
<223> OTHER INFORMATION: PCR primer (L1F6)

<400> SEQUENCE: 71
cgtaaacgtt ttccatattt tttt                                            24

<210> SEQ ID NO 72
<211> LENGTH: 21
<212> TYPE: DNA
<213> ORGANISM: artificial sequence
<220> FEATURE:
<223> OTHER INFORMATION: PCR primer (L1R3)

<400> SEQUENCE: 72
cagtacagag tttttagagt g                                               21

<210> SEQ ID NO 73
<211> LENGTH: 24
<212> TYPE: DNA
<213> ORGANISM: artificial sequence
<220> FEATURE:
<223> OTHER INFORMATION: PCR primer (L1C1)

<400> SEQUENCE: 73
cgtaaacgtt ttccctatttt tttt                                           24

<210> SEQ ID NO 74
<211> LENGTH: 21

```
<212> TYPE: DNA
<213> ORGANISM: artificial sequence
<220> FEATURE:
<223> OTHER INFORMATION: PCR primer (L1C2)

<400> SEQUENCE: 74
caatacagag tatttagggt a                                              21

<210> SEQ ID NO 75
<211> LENGTH: 21
<212> TYPE: DNA
<213> ORGANISM: artificial sequence
<220> FEATURE:
<223> OTHER INFORMATION: PCR primer (new L1C2)

<400> SEQUENCE: 75
caatataggg tatttagggt a                                              21

<210> SEQ ID NO 76
<211> LENGTH: 23
<212> TYPE: DNA
<213> ORGANISM: Human papillomavirus type 6
<220> FEATURE:
<221> NAME/KEY: misc_feature
<223> OTHER INFORMATION: HPV-6 amplicon genus-specific probe binding
      site

<400> SEQUENCE: 76
cgcaccaaca tattttatca tgc                                            23

<210> SEQ ID NO 77
<211> LENGTH: 39
<212> TYPE: DNA
<213> ORGANISM: Human papillomavirus type 6
<220> FEATURE:
<221> NAME/KEY: misc_feature
<223> OTHER INFORMATION: HPV-6 amplicon type-specific probe binding site

<400> SEQUENCE: 77
ccttattttt ccataaaacg ggctaacaaa actgttgtg                           39

<210> SEQ ID NO 78
<211> LENGTH: 23
<212> TYPE: DNA
<213> ORGANISM: Human papillomavirus type 11
<220> FEATURE:
<221> NAME/KEY: misc_feature
<223> OTHER INFORMATION: HPV-11 amplicon genus-specific probe binding
      site

<400> SEQUENCE: 78
cgcaccaaca tattttatca tgc                                            23

<210> SEQ ID NO 79
<211> LENGTH: 39
<212> TYPE: DNA
<213> ORGANISM: Human papillomavirus type 11
<220> FEATURE:
<221> NAME/KEY: misc_feature
<223> OTHER INFORMATION: HPV-11 amplicon type-specific probe binding
      site

<400> SEQUENCE: 79
ccatattact ctatcaaaaa agttaacaaa acagttgta                           39

<210> SEQ ID NO 80
<211> LENGTH: 23
```

```
<212> TYPE: DNA
<213> ORGANISM: Human papillomavirus type 42
<220> FEATURE:
<221> NAME/KEY: misc_feature
<223> OTHER INFORMATION: HPV-42 amplicon genus-specific probe binding
      site

<400> SEQUENCE: 80
cgcaccaact acttttacca tgc                                              23

<210> SEQ ID NO 81
<211> LENGTH: 42
<212> TYPE: DNA
<213> ORGANISM: Human papillomavirus type 42
<220> FEATURE:
<221> NAME/KEY: misc_feature
<223> OTHER INFORMATION: HPV-42 amplicon type-specific probe binding
      site

<400> SEQUENCE: 81
ccttattact ctattacaaa aagccaaata agacatctat cc                         42

<210> SEQ ID NO 82
<211> LENGTH: 23
<212> TYPE: DNA
<213> ORGANISM: Human papillomavirus type 44
<220> FEATURE:
<221> NAME/KEY: misc_feature
<223> OTHER INFORMATION: HPV-44 amplicon genus-specific probe binding
      site

<400> SEQUENCE: 82
cgcaccaaca tatattacca tgc                                              23

<210> SEQ ID NO 83
<211> LENGTH: 39
<212> TYPE: DNA
<213> ORGANISM: Human papillomavirus type 44
<220> FEATURE:
<221> NAME/KEY: misc_feature
<223> OTHER INFORMATION: HPV-44 amplicon type-specific probe binding
      site

<400> SEQUENCE: 83
ccttattttg ccatcgacc agcaaacaag acacttgtg                              39

<210> SEQ ID NO 84
<211> LENGTH: 23
<212> TYPE: DNA
<213> ORGANISM: Human papillomavirus type 16
<220> FEATURE:
<221> NAME/KEY: misc_feature
<223> OTHER INFORMATION: HPV-16 amplicon genus-specific probe binding
      site

<400> SEQUENCE: 84
cgcacaaaca tatattatca tgc                                              23

<210> SEQ ID NO 85
<211> LENGTH: 40
<212> TYPE: DNA
<213> ORGANISM: Human papillomavirus type 16
<220> FEATURE:
<221> NAME/KEY: misc_feature
<223> OTHER INFORMATION: HPV-16 amplicon type-specific probe binding
      site

<400> SEQUENCE: 85
```

-continued ttttcctatt aaaaaaccta acaataacaa aatattagtt                    40

<210> SEQ ID NO 86
<211> LENGTH: 23
<212> TYPE: DNA
<213> ORGANISM: Human papillomavirus type 18
<220> FEATURE:
<221> NAME/KEY: misc_feature
<223> OTHER INFORMATION: HPV-18 amplicon genus-specific probe binding
      site

<400> SEQUENCE: 86
cccacaagca tattttatca tgc                                     23

<210> SEQ ID NO 87
<211> LENGTH: 41
<212> TYPE: DNA
<213> ORGANISM: Human papillomavirus type 18
<220> FEATURE:
<221> NAME/KEY: misc_feature
<223> OTHER INFORMATION: HPV-18 amplicon type-specific probe binding
      site

<400> SEQUENCE: 87
attttagggt tcctgcaggt ggtggcaata agcaggatat t                 41

<210> SEQ ID NO 88
<211> LENGTH: 23
<212> TYPE: DNA
<213> ORGANISM: Human papillomavirus type 31
<220> FEATURE:
<221> NAME/KEY: misc_feature
<223> OTHER INFORMATION: HPV-31 amplicon genus-specific probe binding
      site

<400> SEQUENCE: 88
cgaaccaaca tatattatca cgc                                     23

<210> SEQ ID NO 89
<211> LENGTH: 40
<212> TYPE: DNA
<213> ORGANISM: Human papillomavirus type 31
<220> FEATURE:
<221> NAME/KEY: misc_feature
<223> OTHER INFORMATION: HPV-31 amplicon type-specific probe binding
      site

<400> SEQUENCE: 89
ttccatacct aaatctgaca atcctaaaaa aatagttgta                   40

<210> SEQ ID NO 90
<211> LENGTH: 23
<212> TYPE: DNA
<213> ORGANISM: Human papillomavirus type 33
<220> FEATURE:
<221> NAME/KEY: misc_feature
<223> OTHER INFORMATION: HPV-33 amplicon genus-specific probe binding
      site

<400> SEQUENCE: 90
cgcacaagca tttattatta tgc                                     23

<210> SEQ ID NO 91
<211> LENGTH: 40
<212> TYPE: DNA
<213> ORGANISM: Human papillomavirus type 33
<220> FEATURE:
<221> NAME/KEY: misc_feature
<223> OTHER INFORMATION: HPV-33 amplicon type-specific probe binding
      site

<400> SEQUENCE: 91
ttctattaaa aatcctacta acgctaaaaa attattggta                              40

<210> SEQ ID NO 92
<211> LENGTH: 23
<212> TYPE: DNA
<213> ORGANISM: Human papillomavirus type 35
<220> FEATURE:
<221> NAME/KEY: misc_feature
<223> OTHER INFORMATION: HPV-35 amplicon genus-specific probe binding
      site

<400> SEQUENCE: 92
cgcacaaaca tctactatca tgc                                               23

<210> SEQ ID NO 93
<211> LENGTH: 40
<212> TYPE: DNA
<213> ORGANISM: Human papillomavirus type 35
<220> FEATURE:
<221> NAME/KEY: misc_feature
<223> OTHER INFORMATION: HPV-35 amplicon type-specific probe binding
      site

<400> SEQUENCE: 93
ctatgctatt aaaaaacaag attctaataa aatagcagta                             40

<210> SEQ ID NO 94
<211> LENGTH: 23
<212> TYPE: DNA
<213> ORGANISM: Human papillomavirus type 39
<220> FEATURE:
<221> NAME/KEY: misc_feature
<223> OTHER INFORMATION: HPV-39 amplicon genus-specific probe binding
      site

<400> SEQUENCE: 94
cgcacaggca tatattatta tgc                                               23

<210> SEQ ID NO 95
<211> LENGTH: 41
<212> TYPE: DNA
<213> ORGANISM: Human papillomavirus type 39
<220> FEATURE:
<221> NAME/KEY: misc_feature
<223> OTHER INFORMATION: HPV-39 amplicon type-specific probe binding
      site

<400> SEQUENCE: 95
attttaaagt gggtatgaat ggtggtcgca agcaggacat t                           41

<210> SEQ ID NO 96
<211> LENGTH: 23
<212> TYPE: DNA
<213> ORGANISM: Human papillomavirus type 45
<220> FEATURE:
<221> NAME/KEY: misc_feature
<223> OTHER INFORMATION: HPV-45 amplicon genus-specific probe binding
      site

<400> SEQUENCE: 96
cgcacaagca tattttatca tgc                                               23

<210> SEQ ID NO 97

```
<211> LENGTH: 40
<212> TYPE: DNA
<213> ORGANISM: Human papillomavirus type 45
<220> FEATURE:
<221> NAME/KEY: misc_feature
<223> OTHER INFORMATION: HPV-45 amplicon type-specific probe binding
      site

<400> SEQUENCE: 97
tagggttgta cctaatggtg caggtaataa acaggctgtt                              40

<210> SEQ ID NO 98
<211> LENGTH: 23
<212> TYPE: DNA
<213> ORGANISM: Human papillomavirus type 51
<220> FEATURE:
<221> NAME/KEY: misc_feature
<223> OTHER INFORMATION: HPV-51 amplicon genus-specific probe binding
      site

<400> SEQUENCE: 98
cgcaccggca tatattacta tgc                                                23

<210> SEQ ID NO 99
<211> LENGTH: 40
<212> TYPE: DNA
<213> ORGANISM: Human papillomavirus type 51
<220> FEATURE:
<221> NAME/KEY: misc_feature
<223> OTHER INFORMATION: HPV-51 amplicon type-specific probe binding
      site

<400> SEQUENCE: 99
ctattttcca atacctaaaa cctcaacgcg tgctgctatt                              40

<210> SEQ ID NO 100
<211> LENGTH: 23
<212> TYPE: DNA
<213> ORGANISM: Human papillomavirus type 52
<220> FEATURE:
<221> NAME/KEY: misc_feature
<223> OTHER INFORMATION: HPV-52 amplicon genus-specific probe binding
      site

<400> SEQUENCE: 100
cgcacaagca tctattatta tgc                                                23

<210> SEQ ID NO 101
<211> LENGTH: 41
<212> TYPE: DNA
<213> ORGANISM: Human papillomavirus type 52
<220> FEATURE:
<221> NAME/KEY: misc_feature
<223> OTHER INFORMATION: HPV-52 amplicon type-specific probe binding
      site

<400> SEQUENCE: 101
taaaaacacc agtagtggta atggtaaaaa agttttagtt c                            41

<210> SEQ ID NO 102
<211> LENGTH: 23
<212> TYPE: DNA
<213> ORGANISM: Human papillomavirus type 56
<220> FEATURE:
<221> NAME/KEY: misc_feature
<223> OTHER INFORMATION: HPV-56 amplicon genus-specific probe binding
      site

<400> SEQUENCE: 102
```

```
cgcactagta tattttatca tgc                                    23

<210> SEQ ID NO 103
<211> LENGTH: 41
<212> TYPE: DNA
<213> ORGANISM: Human papillomavirus type 56
<220> FEATURE:
<221> NAME/KEY: misc_feature
<223> OTHER INFORMATION: HPV-56 amplicon type-specific probe binding
      site

<400> SEQUENCE: 103
ctattactct gtgactaagg acaataccaa aacaaacatt c                 41

<210> SEQ ID NO 104
<211> LENGTH: 23
<212> TYPE: DNA
<213> ORGANISM: Human papillomavirus type 58
<220> FEATURE:
<221> NAME/KEY: misc_feature
<223> OTHER INFORMATION: HPV-58 amplicon genus-specific probe binding
      site

<400> SEQUENCE: 104
cgcacaagca tttattatta tgc                                    23

<210> SEQ ID NO 105
<211> LENGTH: 41
<212> TYPE: DNA
<213> ORGANISM: Human papillomavirus type 58
<220> FEATURE:
<221> NAME/KEY: misc_feature
<223> OTHER INFORMATION: HPV-58 amplicon type-specific probe binding
      site

<400> SEQUENCE: 105
ttccatcaaa agtcccaata acaataaaaa agtattagtt c                 41

<210> SEQ ID NO 106
<211> LENGTH: 23
<212> TYPE: DNA
<213> ORGANISM: Human papillomavirus type 59
<220> FEATURE:
<221> NAME/KEY: misc_feature
<223> OTHER INFORMATION: HPV-59 amplicon genus-specific probe binding
      site

<400> SEQUENCE: 106
cgtaccagta ttttctacca cgc                                    23

<210> SEQ ID NO 107
<211> LENGTH: 41
<212> TYPE: DNA
<213> ORGANISM: Human papillomavirus type 59
<220> FEATURE:
<221> NAME/KEY: misc_feature
<223> OTHER INFORMATION: HPV-59 amplicon type-specific probe binding
      site

<400> SEQUENCE: 107
ttttaaagta cctaaaggtg gtaatggtag acaggatgtt c                 41

<210> SEQ ID NO 108
<211> LENGTH: 23
<212> TYPE: DNA
<213> ORGANISM: Human papillomavirus type 66
<220> FEATURE:
```

```
<221> NAME/KEY: misc_feature
<223> OTHER INFORMATION: HPV-66 amplicon genus-specific probe binding
      site

<400> SEQUENCE: 108
cgtaccagta tattttatca tgc                                              23

<210> SEQ ID NO 109
<211> LENGTH: 41
<212> TYPE: DNA
<213> ORGANISM: Human papillomavirus type 66
<220> FEATURE:
<221> NAME/KEY: misc_feature
<223> OTHER INFORMATION: HPV-66 amplicon type-specific probe binding
      site

<400> SEQUENCE: 109
ttattactct gtttccaaat ctggtaccaa acaaacatc c                           41

<210> SEQ ID NO 110
<211> LENGTH: 23
<212> TYPE: DNA
<213> ORGANISM: Human papillomavirus type 68
<220> FEATURE:
<221> NAME/KEY: misc_feature
<223> OTHER INFORMATION: HPV-68 amplicon genus-specific probe binding
      site

<400> SEQUENCE: 110
cgcactggca tgtattacta tgc                                              23

<210> SEQ ID NO 111
<211> LENGTH: 40
<212> TYPE: DNA
<213> ORGANISM: Human papillomavirus type 68
<220> FEATURE:
<221> NAME/KEY: misc_feature
<223> OTHER INFORMATION: HPV-68 amplicon type-specific probe binding
      site

<400> SEQUENCE: 111
ttttaaggtt cctatgtctg ggggccgcaa gcagggcatt                            40

<210> SEQ ID NO 112
<211> LENGTH: 244
<212> TYPE: DNA
<213> ORGANISM: Human papillomavirus type 44
<220> FEATURE:
<221> NAME/KEY: misc_feature
<223> OTHER INFORMATION: HPV-44 amplicon

<400> SEQUENCE: 112
cgtaaacgtg tttccttgtt ttttgcagat gtggcggcct agtgaaaacc aggtatatgt      60
gcctcctccc gccccagtat ccaaagtaat acctacggat gcctatgtca aacgcaccaa     120
catatattac catgctagca gttctagact tcttgctgtg ggcaacccctt attttgccat    180 acgaccagca acaagacac ttgtgcctaa ggtttcggga tttcaatata gggttttttaa     240 gatg                                                                  244

<210> SEQ ID NO 113
<211> LENGTH: 253
<212> TYPE: DNA
<213> ORGANISM: Human papillomavirus type 35
<220> FEATURE:
<221> NAME/KEY: misc_feature
<223> OTHER INFORMATION: HPV-35 amplicon
```

<400> SEQUENCE: 113

```
cgtaaagcta tcccatattt ttttgcagat gtctctgtgg cggtctaacg aagccactgt      60
ctacctgcct ccagtgtcag tgtctaaggt tgttagcact gatgaatatg taacacgcac     120
aaacatctac tatcatgcag gcagttctag gctattagct gtgggtcacc catactatgc     180
tattaaaaaa caagattcta ataaaatagc agtacccaag gtatctggtt tgcaatacag     240
agtatttaga gta                                                        253
```

<210> SEQ ID NO 114
<211> LENGTH: 253
<212> TYPE: DNA
<213> ORGANISM: Human papillomavirus type 39
<220> FEATURE:
<221> NAME/KEY: misc_feature
<223> OTHER INFORMATION: HPV-39 amplicon

<400> SEQUENCE: 114

```
cgtaaacgta ttccctattt tttttcagat ggctatgtgg cggtctagtg acagcatggt      60
gtatttgcct ccaccttctg tggcgaaggt tgtcaatact gatgattatg ttacacgcac     120
aggcatatat tattatgctg gcagctctag attattaaca gtaggacatc catattttaa     180
agtgggtatg aatggtggtc gcaagcagga cattccaaag gtgtctgcat atcaatatag     240
ggtatttcgc gtg                                                        253
```

<210> SEQ ID NO 115
<211> LENGTH: 256
<212> TYPE: DNA
<213> ORGANISM: Human papillomavirus type 45
<220> FEATURE:
<221> NAME/KEY: misc_feature
<223> OTHER INFORMATION: HPV-45 amplicon

<400> SEQUENCE: 115

```
cgtaaacgta ttccctattt ttttgcagat ggctttgtgg cggcctagtg acagtacggt      60
atatcttcca ccaccttctg tggccagagt tgtcagcact gatgattatg tgtctcgcac     120
aagcatattt tatcatgcag gcagttcccg attattaact gtaggcaatc catattttag     180
ggttgtacct aatggtgcag gtaataaaca ggctgttcct aaggtatccg catatcagta     240
tagggtgttt agagta                                                     256
```

<210> SEQ ID NO 116
<211> LENGTH: 250
<212> TYPE: DNA
<213> ORGANISM: Human papillomavirus type 51
<220> FEATURE:
<221> NAME/KEY: misc_feature
<223> OTHER INFORMATION: HPV-51 amplicon

<400> SEQUENCE: 116

```
cgtaaacgta taccctattt ttttacagat ggcattgtgg cgcactaatg acagcaaggt      60
gtatttgcca cctgcacctg tgtctcgaat tgtgaataca gaagaatata tcacacgcac     120
cggcatatat tactatgcag gcagttccag actaataaca ttaggacatc cctatttttcc    180
aatacctaaa acctcaacgc gtgctgctat tcctaaagta tctgcatttc aatacagggt     240
atttagggta                                                            250
```

<210> SEQ ID NO 117
<211> LENGTH: 250

```
<212> TYPE: DNA
<213> ORGANISM: Human papillomavirus type 56
<220> FEATURE:
<221> NAME/KEY: misc_feature
<223> OTHER INFORMATION: HPV-56 amplicon

<400> SEQUENCE: 117
cgtaaacgta ttccctattt ttttgcagat ggcgacgtgg cggcctagtg aaaataaggt      60
gtatctacct ccaacacctg tttcaaaggt tgtggcaacg gattcctatg taaaacgcac     120
tagtatattt tatcatgcag gcagttcacg attgcttgcc gtaggacatc cctattactc     180
tgtgactaag gacaatacca aaacaaacat tcccaaagtt agtgcatatc aatatagggt     240
atttagggta                                                            250

<210> SEQ ID NO 118
<211> LENGTH: 253
<212> TYPE: DNA
<213> ORGANISM: Human papillomavirus type 59
<220> FEATURE:
<221> NAME/KEY: misc_feature
<223> OTHER INFORMATION: HPV-59 amplicon

<400> SEQUENCE: 118
ctgaaactgg ttccctattt ttttacagat ggctctatgg cgttctagtg acaacaaggt      60
gtatctacct ccaccttcgg tagctaaggt tgtcagcact gatgagtatg tcacccgtac     120
cagtattttc taccacgcag gcagttccag acttcttaca gttggacatc catatttaa      180 agtacctaaa ggtggtaatg gtagacagga tgttcctaag gtgtctgcat atcaatacag     240
agtatttagg gtt                                                        253

<210> SEQ ID NO 119
<211> LENGTH: 250
<212> TYPE: DNA
<213> ORGANISM: Human papillomavirus type 66
<220> FEATURE:
<221> NAME/KEY: misc_feature
<223> OTHER INFORMATION: HPV-66 amplicon

<400> SEQUENCE: 119
cgtaaacgta ttccctattt ttttgcagat ggcgatgtgg cggcctagtg acaataaggt      60
gtacctacct ccaacacctg tttcaaaggt tgtggcaacg gatacatatg taaaacgtac     120
cagtatattt tatcatgcag gtagctctag gttgcttgct gttggccatc cttattactc     180
tgtttccaaa tctggtacca aaacaaacat ccctaaagtt agtgcatatc agtatagagt     240
gtttagggta                                                            250

<210> SEQ ID NO 120
<211> LENGTH: 253
<212> TYPE: DNA
<213> ORGANISM: Human papillomavirus type 68
<220> FEATURE:
<221> NAME/KEY: misc_feature
<223> OTHER INFORMATION: HPV-68 amplicon

<400> SEQUENCE: 120
cgtaaacacc ttccctattt ttttacagat ggcattgtgg cgagctagcg acaacatggt      60
gtatttgcct cccccctcag tggcgaaggt tgtcaataca gatgattatg tgacacgcac     120
```

```
tggcatgtat tactatgctg gtacatctag gttattaact gtaggccatc catattttaa    180
ggttcctatg tctgggggcc gcaagcaggg cattcctaag gtgtctgcat atcaatacag    240
agtgtttagg gtt                                                       253
```